United States Patent
Pike et al.

(10) Patent No.: US 11,234,453 B2
(45) Date of Patent: Feb. 1, 2022

(54) DISSOLVABLE MICRO-INGREDIENT CONTAINERS AND METHODS FOR PREPARING ANIMAL FEEDS USING SUCH CONTAINERS

(71) Applicant: CAN TECHNOLOGIES, INC., Wayzata, MN (US)

(72) Inventors: Nathan Pike, Amarillo, TX (US); Anna Taylor, St. Michael, MN (US); Steve Bachman, Canyon, TX (US)

(73) Assignee: Can Technologies, Inc., Wayzata, MN (US)

( * ) Notice: Subject to any disclaimer, the term of this patent is extended or adjusted under 35 U.S.C. 154(b) by 360 days.

(21) Appl. No.: 16/095,866

(22) PCT Filed: Apr. 20, 2017

(86) PCT No.: PCT/US2017/028580
§ 371 (c)(1),
(2) Date: Oct. 23, 2018

(87) PCT Pub. No.: WO2017/189322
PCT Pub. Date: Nov. 2, 2017

(65) Prior Publication Data
US 2021/0219576 A1 Jul. 22, 2021

Related U.S. Application Data

(60) Provisional application No. 62/326,973, filed on Apr. 25, 2016.

(51) Int. Cl.
| | | |
|---|---|---|
| A23K 10/18 | (2016.01) | |
| A23K 10/38 | (2016.01) | |
| A23K 20/105 | (2016.01) | |
| A23K 20/111 | (2016.01) | |
| A23K 20/158 | (2016.01) | |
| A23K 20/195 | (2016.01) | |
| A23K 40/00 | (2016.01) | |
| A23K 40/30 | (2016.01) | |
| A23K 50/10 | (2016.01) | |
| A23K 50/20 | (2016.01) | |
| A23K 50/30 | (2016.01) | |
| A23K 50/40 | (2016.01) | |
| A23K 50/75 | (2016.01) | |
| A23K 50/80 | (2016.01) | |
| A61K 31/35 | (2006.01) | |
| A61K 47/32 | (2006.01) | |
| A61K 9/00 | (2006.01) | |
| B65D 65/46 | (2006.01) | |

(52) U.S. Cl.
CPC .............. *A23K 40/00* (2016.05); *A23K 10/38* (2016.05); *A23K 20/105* (2016.05); *A23K 20/158* (2016.05); *A23K 20/195* (2016.05); *A23K 50/10* (2016.05); *A61K 9/009* (2013.01); *A61K 9/0056* (2013.01); *A61K 31/35* (2013.01); *A61K 47/32* (2013.01); *B65D 65/46* (2013.01)

(58) Field of Classification Search
CPC .... A23K 40/00; A23K 20/158; A23K 20/195; A23K 50/10; A23K 10/38; A23K 20/105; A23K 10/18; A23K 20/111; A23K 50/20; A23K 50/75; A23K 50/30; A23K 50/40; A23K 50/80; A23K 40/30; A61K 9/0056; A61K 9/009; A61K 31/35; A61K 47/32; B65D 65/46
See application file for complete search history.

(56) References Cited

U.S. PATENT DOCUMENTS

| | | | |
|---|---|---|---|
| 4,221,818 A | 9/1980 | Schroeder | |
| 4,502,416 A * | 3/1985 | Keysell | ................ A01K 5/0283 119/51.11 |
| 4,731,249 A * | 3/1988 | Findley | ................... A23K 20/26 426/69 |
| 4,803,085 A | 2/1989 | Findley | |
| 6,469,067 B1 | 10/2002 | Bouvier et al. | |
| 7,022,656 B2 | 4/2006 | Verrall et al. | |
| 9,073,294 B2 * | 7/2015 | Kumar | .................... B32B 27/30 |
| 2010/0247507 A1 | 9/2010 | Harz et al. | |
| 2013/0108772 A1 | 5/2013 | Rothamel | |

FOREIGN PATENT DOCUMENTS

| | | |
|---|---|---|
| EP | 0 319 545 | 3/1992 |
| RU | 2398446 | 9/2010 |
| WO | 2002028199 A2 | 4/2002 |

OTHER PUBLICATIONS

International Search Report dated Jul. 5, 2017 for PCTUS2017/028580 filed Apr. 20, 2017 (3 pages).
International Search Report dated May 23, 2018 for POTUS2017/068721 filed Dec. 28, 2017 (3 pages).

\* cited by examiner

*Primary Examiner* — Trevor Love
(74) *Attorney, Agent, or Firm* — Foley & Lardner LLP

(57) ABSTRACT

The present invention relates to dissolvable containers for animal feed micro-ingredients, and methods for using such dissolvable containers to prepare an animal feed mixture. Ingredients required in very small amounts with respect to the rest of the components in an animal feed, i.e., micro-ingredients, can be pre-measured and sealed within the dissolvable containers, which can be made from a water-soluble polymer film, then added to the other feed components when the complete animal feed is being prepared.

8 Claims, No Drawings

DISSOLVABLE MICRO-INGREDIENT CONTAINERS AND METHODS FOR PREPARING ANIMAL FEEDS USING SUCH CONTAINERS

CROSS-REFERENCE TO RELATED APPLICATIONS

This application is a national phase application of PCT/US2017/028580, filed Apr. 20, 2017, which claims the benefit of U.S. Provisional Patent Application No. 62/326,973, filed Apr. 25, 2016, each of which is hereby incorporated by reference in its entirety.

BACKGROUND

Animal feeds, for example feeds for livestock such as cattle, often require a mixture of components in relatively large amounts, such as protein, starch, and fiber, combined with other components that must be administered to the animal in much smaller amounts. For example, some additives used for improving weight gain and feed efficiency can be required in amounts as small as a few milligrams per ton of complete feed. Administering an excessively high concentration of these additives can cause harmful side effects in an animal. However, mixing small amounts of such additives into the feed such that the additives are homogenously dispersed in the complete feed can be problematic. Current equipment and practices used to mix these additives into animal feeds can be expensive, inaccurate, inconvenient, or unreliable.

SUMMARY OF THE INVENTION

Described herein are methods, compositions, and devices related to sealing micro-ingredients within a container made from a water-soluble film for the purpose of administering the micro-ingredients to an animal. In one aspect, the methods can be used to prepare animal feed mixtures containing micro-ingredient(s). In one aspect, the micro-ingredient(s) are dispersed substantially homogenously throughout the animal feed mixture. The animal feed mixtures can be composed primarily of solids, or the animal feed mixtures can be a solution, suspension, or slurry. Further, the animal feed mixtures can be used to feed any type of animal, including livestock, poultry, aquaculture, and pets.

In one aspect, the method is a method for preparing an animal feed mixture, comprising: providing a container comprising a water-soluble film, wherein a micro-ingredient is sealed within the container, adding the container to a feed mixer or vessel with one or more feed components, wherein the one or more feed components have a moisture content suitable for dissolving the water-soluble film, and mixing the container with the one or more feed components in the feed mixer or vessel wherein at least a portion of the water-soluble film dissolves during mixing to release the micro-ingredient, and the micro-ingredient is combined with the one or more feed components to form an animal feed mixture. In some embodiments, one or more additional micro-ingredients are sealed within the container prior to mixing. In some embodiments, the method further comprises adding one or more additional micro-ingredient containers to the feed mixer or vessel. In some such embodiments, each micro-ingredient container comprises a different micro-ingredient.

In one aspect, the method is a method for preparing an animal feed mixture, comprising: providing a container comprising a water-soluble film, wherein a micro-ingredient is sealed within the container, and adding the container and water to a liquid feed tank or vessel, wherein at least a portion of the water-soluble film dissolves in the liquid feed tank or vessel to release the micro-ingredient to form a substantially homogenous animal feed mixture comprising water and the micro-ingredient. In some embodiments, the method further comprises adding one or more feed components to the liquid feed tank or vessel. In some embodiments, the method further comprises agitating the animal feed mixture. In some embodiments, the animal feed mixture is a solution of the micro-ingredient in water. In some embodiments, the animal feed mixture is a milk replacement, a milk supplement, a colostrum replacement, or a colostrum supplement. In some embodiments, the method further comprises spraying the animal feed mixture onto an animal feed material or otherwise combining the animal feed mixture with other animal feed materials.

The methods and containers can be used in connection with any type of animal feed. In some embodiments, the one or more feed components comprise protein, carbohydrate, fat, fiber, or a mixture thereof. In some embodiments, the moisture content of the animal feed mixture is in the range of about 20 to 60%, or in the range of about 20 to 80%.

In one aspect, the method is a method of packaging a micro-ingredient for use in an animal feed mixture, comprising: measuring a pre-determined amount of one or more micro-ingredients, dispensing the one or more micro-ingredients into a dissolvable container, and sealing the dissolvable container. In some embodiments, the method further comprises mixing the one or more micro-ingredients with a carrier or excipient prior to dispensing the one or more micro-ingredients into the dissolvable container. In some embodiments, the one or more micro-ingredients are measured and/or dispensed in a low moisture environment. In some embodiments, the one or more micro-ingredients are measured and/or dispensed in a low oxygen environment. In some embodiments, the method further comprises transferring the sealed dissolvable container to a secondary container.

In one aspect, the methods described herein further comprise feeding an animal with the animal feed mixture. In one aspect, the method is a method for administering a micro-ingredient to an animal, comprising: feeding a dissolvable container comprising a micro-ingredient to an animal.

In one aspect, the present invention relates to a dissolvable animal feed container, comprising: a water-soluble film, wherein the film forms a sealed compartment, and one or more micro-ingredients contained within the sealed compartment. In some embodiments, the dissolvable container comprises a water-soluble film. In some embodiments, the water-soluble film comprises a polyvinyl alcohol. In some embodiments, the water-soluble film is suitable for ingestion by an animal. In some embodiments, the container has multiple compartments suitable for containing a different micro-ingredient or micro-ingredient mixture within each compartment.

Any suitable type or amount of micro-ingredient can be used with the methods and containers described herein. In some embodiments, the micro-ingredient is a pharmaceutical composition. In some embodiments, the pharmaceutical composition is selected from the group consisting of a steroid, a beta-agonist, an antibiotic, and a vaccine. In some embodiments, the micro-ingredient is a microbe. In some embodiments, the microbe is a bacteria. In some embodiments, the microbe is a yeast. In some embodiments, the micro-ingredient is an essential oil. In some embodiments, the micro-ingredient is a plant extract. In some embodiments, the micro-ingredient is an ionophore. In some embodiments, the micro-ingredient is a vitamin. In some embodiments, the one or more micro-ingredients are present in an amount suitable to feed multiple animals. In some embodiments, the amount of micro-ingredient packaged within the container is about 1 kg or less, about 100 g or less, about 10 g or less, or about 1 g or less. In some embodiments, the micro-ingredient is a liquid. In some embodiments, the micro-ingredient is a solid.

In one aspect, materials other than micro-ingredients can be packaged in the dissolvable containers described herein. In some embodiments, a carrier or excipient is mixed with the micro-ingredient prior to sealing within the container.

In some embodiments, the ratio of the micro-ingredient to the total amount of animal feed mixture is about 1:100 or less, about 1:1000 or less, or about 1:10,000 or less. In some embodiments, the concentration of the micro-ingredient is less than about 0.1%, less than about 0.01%, less than about 0.001%, or less than about 0.0001%.

The elements or aspects of any embodiment of the methods, compositions, or devices described above can be applied to any other embodiment, as would be understood by a person skilled in the art.

DETAILED DESCRIPTION

It is to be understood that the figures and descriptions of the present invention provided herein have been simplified to illustrate elements that are relevant for a clear understanding of the present invention, while eliminating other elements found in the related field(s) of art. Those of ordinary skill in the art would recognize that other elements or steps may be desirable or required in implementing the present invention. However, because such elements or steps are well known in the art or do not facilitate a better understanding of the present invention, a discussion of such elements or steps is not provided herein.

Unless defined otherwise, all technical and scientific terms used herein have the same meaning as commonly understood by one of ordinary skill in the art to which this invention belongs. As used herein, each of the following terms has the meaning associated with it as defined in this section.

The term "micro-ingredient" as used herein refers to an animal feed ingredient that is generally used in very small amounts with respect to the complete animal feed. Exemplary micro-ingredients include, but are not limited to: pharmaceutical compounds, such as beta-agonists, steroids, antibiotics, and ionophores; vaccines; microbes, such bacterial inoculants, bacteriophages, and yeasts; enzymes; plant extracts; trace minerals; vitamins; dyes or tracers; and plant extracts or essential oils.

The terms "animal feed," "feed mixture," "animal feed mixture," "complete animal feed," and the like, are used interchangeably herein, and refer to a mixture of feed components or ingredients that is suitable for administering to an animal. As contemplated herein, a complete animal feed includes at least a significant portion, if not all, of an animal's dietary needs.

Throughout this disclosure, various aspects of the invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 7 should be considered to have specifically disclosed subranges such as from 1 to 3, from 1 to 4, from 1 to 6, from 2 to 5, from 3 to 5, etc., as well as individual numbers within that range, for example, 1, 2, 3, 3.6, 4, 5, 5.8, 6, 7, and any whole and partial increments in between. This applies regardless of the breadth of the range.

Method of Preparing an Animal Feed

Described herein are dissolvable containers for animal feed micro-ingredients, and methods for using such dissolvable containers to prepare an animal feed mixture. Ingredients required in very small amounts with respect to the rest of the components in an animal feed, i.e., micro-ingredients, can be pre-measured and sealed within the dissolvable containers, which can be made from a water-soluble polymer film, then added to the other feed components when the complete animal feed is being prepared. For example, the pre-packaged micro-ingredient containers can be added to mixing equipment along with the rest of the ingredients in an animal feed. Since feed ingredients suitable for feeding animals often include a significant amount of moisture, the water-soluble film of the micro-ingredient containers can readily dissolve during the mixing process. As a result, the micro-ingredients are released into the other feed components during mixing, such that the micro-ingredients are thoroughly dispersed throughout the animal feed. In one embodiment, the agitation and grinding action caused by mixing the other feed components can aid in rupturing the dissolvable container, resulting in more rapid release of the micro-ingredients and dissolution of the water-soluble film.

The methods described herein can eliminate the need for expensive or unreliable measuring and dispensing equipment at the location where the animal feed is prepared and used. Further, the use of the pre-packaged containers can prevent the micro-ingredients from degrading or being contaminated prior to use by sealing these ingredients within a water-soluble film.

Pharmaceutical compounds, inoculants, and other materials are often required in much smaller amounts compared to other nutrients or ingredients needed in animal feed, such as protein, fiber, and carbohydrates. It is contemplated herein that such low-dose ingredients often require relatively high-precision measurement for addition to an animal feed. Incorrect measurement or dispensing of such micro-ingredients can result in negative health effects on animals ingesting the resultant feed, or can add unnecessary costs. Further, such micro-ingredient materials need to be well-blended with the major feed ingredients to prevent localized concentration differences. Such localized concentrations of micro-ingredients can result in a small number of animals consuming a disproportionate amount of a micro-ingredient, i.e., some animals will receive a high dose of an ingredient while other animals may receive too little, if any, of that same ingredient. The containers described herein can be useful for ensuring micro-ingredients are properly measured and then thoroughly mixed with the rest of the animal feed.

Currently, in some cases, micro-ingredients are measured using expensive balances and/or dispensers. For example, "micromachines" are often used to prepare animal feed in large livestock feedlots with 10,000 head of livestock or more. These devices have several micro-ingredient bins in which various feed additives are stored. Batching software is used to communicate to the device which additive and how much additive is required in each batch of feed. The device then weighs the desired amount of each additive needed for a batch, mixes the additives in a water slurry, and pumps the additive slurry mix into the total mixed ration (TMR). However, micromachines are typically very expensive, and therefore are not often used by smaller feedlots that are unable to leverage the cost of the devices compared to the number of animals on the feedlot.

In other cases, micro-ingredients are measured using relatively inaccurate or unreliable methods, such as measuring the micro-ingredients by volume using a scoop. In addition, measuring and dispensing micro-ingredients can expose the micro-ingredients to air or moisture, which can decrease the shelf-life of the micro-ingredients. In some cases, currently used methods for measuring and dispensing micro-ingredients can often waste micro-ingredients because of spillage. In addition, some micro-ingredient materials can be harmful or unhealthy to anyone who regularly handles such materials, for example due to the potential for exposure to relatively large amounts of such materials via breathing of dust.

The methods of the present invention can address these issues by measuring and pre-packaging micro-ingredients in sealed containers. The sealed micro-ingredient containers can be prepared at a separate facility from where the animals are fed. Such a facility can use relatively high-precision measuring equipment while minimizing exposure of the micro-ingredients to air, moisture, and/or contaminants via environmental controls. These methods can also prevent or minimize the potential for human exposure to such micro-ingredients. The pre-packaged single-use containers of micro-ingredients can then be stored in secondary containers and shipped to the feed location until needed for use. The pre-packaged containers can eliminate the need for livestock producers to buy and maintain expensive dispensing equipment, can reduce the potential for error in measuring and using the micro-ingredients, and can reduce or eliminate the waste of micro-ingredients by providing a more controlled storage environment.

In some embodiments, the dissolvable container is a pouch made of a relatively thin water-soluble polymer film. The container can be loaded with a predetermined amount of a micro-ingredient and then sealed. The container can then be added to equipment used to prepare feed for an animal. For example, the container can be added to a mixer or auger that is used to prepare a feed mixture for an animal. Such feed mixtures typically include a significant amount of moisture, for example 20 to 80% moisture. Therefore, the moisture present in certain components of the feed mixture can be sufficient to dissolve the water-soluble polymer film of the micro-ingredient container, which can allow the contents of the container to be released and dispersed in the feed mixture. In some embodiments, water can be added to the feed mixture to facilitate or accelerate dissolution of the water-soluble film.

In some cases, micro-ingredients are dissolved or dispersed in water and then sprayed onto a feed mixture. Accordingly, in some embodiments, the dissolvable micro-ingredient container can be added to an applicator tank, where the micro-ingredient container is combined with water to dissolve the film, and the resulting micro-ingredient solution is then sprayed onto or otherwise added to the feed mixture.

However, any technique for dissolving the water-soluble film of the micro-ingredient container, and then combining the micro-ingredient container contents with the feed mixture, can be used. Further, it is contemplated herein that the complete dissolution of the water-soluble film is not required, and the micro-ingredient container can be only partially dissolved to adequately release the micro-ingredients into the feed mixture.

The containers described herein can also be used to deliver micro-ingredients in liquid feed applications, i.e., situations in which feed components are administered to an animal via a liquid instead of a solid feed. In some embodiments, micro-ingredients, such as drugs, vitamins, bloat preventatives, dewormers, etc., can be added to watering troughs via the containers described herein for administering such micro-ingredients to animals. This method of administering micro-ingredients can be particularly useful for non-confined/pasture or range cattle. The containers can also be used to deliver feed additives to animals, such as pets or horses, which drink from a container. In some embodiments, the containers can be used to administer micro-ingredients or other additives in milk, milk replacers, colostrum, or similar feed materials. In any of the above embodiments, other feed ingredients or components can be added to the liquid feed in addition to one or more micro-ingredients to form a multi-component feed solution.

In some embodiments, the ingredients useful for packaging in the containers described herein can be ingredients that are sensitive to oxygen, moisture, light, or other environmental conditions. By encapsulating such ingredients in the containers described herein, the shelf-life of these ingredients can be increased, or the need for providing protective storage conditions can be minimized or avoided. In addition, such ingredients can be pre-packaged in the dissolvable containers in a controlled facility, thus reducing the chance of contamination or degradation of these ingredients that can occur when the ingredients are weighed out and dispensed prior to feeding. Further, the dissolvable containers described herein are also useful for ingredients that are undesirable to be handled directly by feed preparers, such as pharmaceutical compounds that can cause health problems in humans. Accordingly, ingredients that would not be considered a low-dose ingredient can also be packaged within the dissolvable containers, for example any ingredient that is sensitive to air or moisture, or any ingredient that can cause adverse health effects in humans when handled regularly and/or handled in large amounts.

The present invention provides other advantages over currently used methods. For example, desiccants or moisture scavengers are often currently added to certain micro-ingredients, such as inoculants, to extend the shelf-life of the micro-ingredients. Such moisture scavengers are insoluble in water and will settle out of solution when the micro-ingredients are used in aqueous solution applicators. By sealing the micro-ingredients in the dissolvable containers described herein, the need for moisture scavengers, or other materials used to increase shelf-life, can be reduced or eliminated.

Another advantage is improved dosing accuracy by eliminating the use of volumetric scoops or other inaccurate measurement methods. The measurement of micro-ingredients is preferably done by mass or weight to eliminate variability caused by air pockets or density variances in the micro-ingredients. The present methods enable the micro-ingredients to be pre-weighed and packaged by someone other than the livestock producer, for example a micro-ingredient manufacturer, thereby eliminating the need for the livestock producer to own and maintain weighing equipment, and/or eliminating the use of inaccurate volumetric scoops by the livestock producer.

In other currently used methods, pre-mixed supplements are used to deliver additives such as micro-ingredients to the feed ration. Typically, supplements are made by third party feed mills. These supplements generally contain vitamins, minerals and protein. Supplements are added to the TMR at 2 to 7% inclusions to balance the diet. Additives are often added to these supplements as the delivery mechanism to the TMR. The method works well in scenarios where the cattle in a facility are uniform and the additive is being applied to all cattle at similar rates. However, when additives are different by various cattle groups in a facility, more supplements are required. These increases inventory costs of the operation.

Yet another advantage is that the containers described herein can be used to provide useful, manageable amounts of single micro-ingredients instead of the commonly used practice of providing a "ration supplement" that contains multiple micro-ingredients. Such a ration supplement is often a mixture of protein, minerals, and the like in combination with one or more micro-ingredients. However, the inclusion rate of any single ingredient in the ration supplement is fixed, and therefore the dosage of any single ingredient in the ration supplement cannot be manipulated without changing the overall balance of all of the ingredients in the ration supplement. Changing the overall balance of the ingredients in an animal feed can have undesirable consequences. Further, most facilities have limited storage for feed supplements, and therefore storing multiple types of ration supplements can be undesirable or impractical. Therefore, the currently used ration supplements greatly limit the flexibility of animal feeders. However, the containers of the present invention can allow animal feeders to maintain an inventory of relatively small amounts of micro-ingredients in discrete containers. This can enable the animal feeder to choose the amount and type of each micro-ingredient separately, which can greatly improve flexibility and convenience in choosing the contents of the animal feed.

Micro-Ingredients

The dissolvable containers can be useful for packaging a variety of ingredients. In some embodiments, the micro-ingredients can be any ingredient that is typically provided in a low-dose on a per animal basis, and therefore needs to be provided in relatively small amounts compared to other feed ingredients. Non-limiting examples of the ratio of a micro-ingredient to the complete animal feed include about 1:10, 1:100, 1:1000 (1 kg per metric ton), 1:10,000, 1:100,000, or 1:1,000,000 (1 part per million). In some embodiments, the ingredients useful for packaging in the dissolvable containers are any ingredients that are desired to be protected from moisture, air, light, contaminants, and/or human contact, regardless of the amount of ingredient that will be added to the feed mixture. In some embodiments, ingredients can be packaged in the dissolvable containers for reasons of convenience. Accordingly, in some embodiments, relatively large amounts of an ingredient can be packaged and used in the dissolvable containers, for example but not limited to, an amount corresponding to greater than 1%, 2%, 5%, 10%, 15%, 20%, 25%, or more of the complete animal feed. The micro-ingredients can be provided as liquids, solids, or a mixture thereof, for packaging in the dissolvable containers.

Micro-ingredients can be added to animal feed for a number of reasons, for example, but not limited to: treatment or prevention of disease, increasing weight gain, improving feed efficiency, suppression of estrus, and increasing carcass leanness. Non-limiting examples of micro-ingredients that can be packaged in the dissolvable containers include: steroids and steroid analogs, such as melengestrol acetate (MGA); antimicrobials, such as tilmicosin phosphate; antibiotics, such as chlortetracycline hydrochloride or tylosin phosphate; beta agonists, such as ractopamine hydrochloride or zilpaterol hydrochloride; and ionophores, such as bambermycins, lasalocid, monensin, or laidlomycin propionate potassium. However, the present invention is not limited to micro-ingredients, and the methods and compositions can include any other type of ingredient. Non-limiting examples of other ingredients that can be packaged in the dissolvable containers include: essential oils, tracer dyes, tannins, pectins, buffers, mycotoxin binders, vitamins, minerals, inoculants, enzymes, amino acids, flavoring agents, pre-biotics, probiotics, bypass fats, milk replacers, milk extenders, colostrum, organic acids, antioxidants, electrolytes, preservatives, and mold inhibitors.

In some embodiments, the containers can also include carriers, dyes, excipients, desiccants, preservatives or other materials in addition to the micro-ingredients. Although the use of the dissolvable containers can eliminate the need for certain materials such as preservatives or desiccants by creating a barrier between the ingredients and the environment, such materials can be used in some embodiments. Such carriers or excipients can be useful to improve the ability for the micro-ingredients to be thoroughly mixed and dispersed throughout the final feed.

It is contemplated that the containers can include a few milligrams or grams of micro-ingredients and/or other materials up to 1 kg, 10 kg, or more. However, the containers can include any suitable amount of micro-ingredients or other materials, and are not limited to any specific size described herein. The amount of micro-ingredients packaged in a single dissolvable container can vary depending on a number of factors. As would be understood by a person skilled in the art, suitable amounts of the micro-ingredients can be packaged in dissolvable containers, based on factors such as the number of animals being fed, the amount of feed being prepared, and the desired dose of a given micro-ingredient. In some embodiments, the micro-ingredients can be packaged in each container in an amount that corresponds to a specific number of animals to be fed, for example 100 cattle. The user of the dissolvable micro-ingredient containers can then use multiple containers, if necessary, to address the specific number of animals to be fed.

Pre-Packaged Micro-Ingredient Containers

Described herein are compositions and methods related to the delivery of animal feed additives or ingredients via a dissolvable container or package. As previously described, the feed additives or ingredients are encased in a water-soluble polymer film that can readily dissolve when exposed to moisture, for example when the container is added to a feed containing sufficient moisture or when the container is consumed by an animal.

An exemplary water-soluble polymer suitable for the present invention is polyvinyl alcohol, but any water-soluble polymer can be used, as would be understood by a person skilled in the art. A description of water-soluble polymers and the use of such polymers in dissolvable pouches is provided in Verrall et al. (U.S. Pat. No. 7,022,656), which is hereby incorporated by reference in its entirety. Further, methods for sealing ingredients inside a water-soluble film are known in the art, for example Kumar et al. (U.S. Pat. No. 9,073,294), which is hereby incorporated by reference in its entirety.

The water-soluble film can be any thickness. Non-limiting examples include 0.5 mm, 1 mm, 1.5 mm, or 2 mm. As would be understood by a person skilled in the art, the thickness of the film can be selected based on the characteristics of the materials to be encapsulated in the container and the end-use application. Accordingly, the container can be relatively soft or flexible, i.e., when the film thickness is relatively thin, or the container can be more rigid, i.e., when a thicker film thickness is used.

The dissolvable containers can also include coatings on the inside or outside surface of the pouch. Such coatings can include additives that serve a number of functions, included but not limited to: protecting the ingredients from UV radiation or surfactants that facilitate the release or dispersal of ingredients from the container.

While it is contemplated herein that most or all of the dissolvable containers are made of a water-soluble polymer, it is contemplated herein that the containers could include other materials, including materials that may not readily dissolve in water. In a preferred embodiment, all materials used in the dissolvable container will be edible or otherwise suitable for consumption by an animal.

In some embodiments, the dissolvable container is a relatively soft thin-film pouch that is generally spherical, or hemispherical in shape. In other embodiments, the container can be some other shape, for example but not limited to, a cylinder or cube.

In some embodiments, the dissolvable container has a single compartment for containing the micro-ingredients. In some embodiments, the dissolvable container can include multiple compartments for keeping different micro-ingredients or micro-ingredient mixtures separate. In some embodiments, the containers can include one or more separate compartments for liquid components and one or more separate compartments for dry or solid components. As contemplated herein, when the container is used to store a liquid component, the container will be suitably modified to prevent premature degradation of the container. For example, if the container is made from a water-soluble polymer and the liquid component contains water, the inside of the container can be coated to prevent contact between the water-soluble polymer and the water in the liquid component. Accordingly, the release of the container's contents can be avoided unless there is suitable mechanical degradation of the container, or a combination of both dissolution of the container and mechanical forces.

In some embodiments, the container can include features that can assist in improving the convenience of use. For example, the container can include a tab, loop, or ring portion that is made of a relatively thick piece of water-soluble polymer. Such a tab or ring portion can be used by a device to pick up and move the container without the need for handling by the user.

In some embodiments, the container can be encapsulated in a non-water soluble film or material that can be removed prior to use. A non-limiting example of such a water-insoluble material is any type of foil. Such non-soluble materials can be used to prevent degradation of the container prior to use. In some embodiments, multiple containers can be packaged in a water-insoluble and/or secondary container for shipment or storage.

In some embodiments, the container can be made of a mixture of water-soluble and non-water soluble materials. In such an embodiment, the container can be configured with non-water soluble materials to delay the release of the container's contents. For example, such a delayed-release version of the container can be useful in an aquaculture application, in which the container contents can be released over an extended period of time to reduce or eliminate the need for adding feed to an animal pond multiple times a day. In another embodiment, an extended-release container can be implemented via other methods, for example by increasing the thickness of the water-soluble container, or by adding coatings to the container that interfere with the dissolution of the water-soluble polymer. In one aspect, the present invention relates to the packaging of micro-ingredients or other materials inside a dissolvable container. An exemplary method for packaging a micro-ingredient in an embodiment of a container described herein includes using a "fill and seal" machine known in the art, for example a system manufactured by Hayssen™ such as the Ultima SV or Simionato Logic S Flexible Systems. The fill and seal machine can be used to package and seal one or more micro-ingredients and any other desired material inside a dissolvable film, such as the Vivos™ film manufactured by Monosol™ Accordingly, in some embodiments, the container of the present invention is a relatively flexible sealed bag or "pod" containing at least one micro-ingredient and any other desired materials. However, the present invention is not limited to any specific methods of packaging; the use of any specific type of fill and seal machine or other packaging system; or any specific embodiment of container described herein, as would be understood by a person skilled in the art.

Method of Feeding an Animal

The present invention also includes a method for feeding animals. In some embodiments, the method includes the steps of providing an embodiment of a micro-ingredient container as described herein, adding the micro-ingredient container to an animal feed mixer with other feed ingredients, mixing the micro-ingredient container with the other feed ingredients such that the contents of the micro-ingredient container are released and thoroughly mixed with the other feed ingredients, then feeding an animal with the combined mixture of feed ingredients and the micro-ingredient.

In some embodiments, the micro-ingredient container can include more than one micro-ingredient. In some embodiments, the method of feeding can include mixing multiple micro-ingredient containers with the other feed ingredients. As contemplated herein, it can be undesirable in some situations to combine certain micro-ingredients, for example due to incompatibility between certain micro-ingredients. Therefore, different micro-ingredients can be prepared in separate containers, as required, and added to the feed mixer immediately prior to feeding the animal.

In some embodiments, the dissolvable micro-ingredient container can be fed directly to an animal rather than dissolving and mixing the container with other ingredients. In such embodiments, the container can dissolve via exposure to moisture in the animal's digestive tract. As would be understood by a person skilled in the art, in such embodiments, the dissolvable container will be sized and shaped to be readily consumed by the targeted animal without causing a choking hazard to the animal.

The dissolvable containers can be used to feed any type of animal. For example, the dissolvable containers can be used to feed livestock, such as cattle and swine; poultry, such as chickens and turkeys; aquaculture animals, such as salmon or shrimp; and companion animals such as dogs, cats, and horses.

EXAMPLES

The invention is further described in detail by reference to the following examples. These examples are provided for purposes of illustration only, and are not intended to be limiting unless otherwise specified. Thus, the invention should in no way be construed as being limited to the

Example 1: Preparation of a Dry Ingredient Animal Feed

Ingredients are sourced and delivered to the production site. Ingredients for feedlots and dairies include but are not limited to corn, wheat, milo, hay, haylage, silage, corn ethanol byproducts, and supplements. Some of these ingredients are relatively high in moisture content (e.g., silage, wet distillers grains, wet corn gluten feed, steam flaked corn). These ingredients are typically stored in commodity bays. The commodity bays are relatively large three-sided, covered structures. Ingredients are transported from a commodity bay to a mixer wagon by wheel loaders. Mixer wagons generally have a load cell and scale read outs on the side of the mixer to assist in measuring out the appropriate amount of each ingredient. The mixer wagons provide the shear and agitation to thoroughly mix and distribute ingredients into the total mixed ration (TMR).

Micro-ingredients are pre-packaged in containers made from a dissolvable film. The film material is suitable for consumption by an animal. The moisture of the ingredients in the ration combined with shear provided by the mixer dissolves and/or erodes the micro-ingredient container film, distributing the micro-ingredient throughout the TMR.

In this example, a 6000 lb. batch of TMR is prepared as a cattle feed. Monensin, an antibiotic micro-ingredient, is desired in the TMR at a concentration of 35 grams per short ton of TMR. An exemplary TMR is made from: 2280 lbs. of steam flaked corn (21% moisture), 2220 lbs. of wet distillers grains (64% moisture), 870 lbs. of wet corn gluten feed (40% moisture), 360 lbs. of Alfalfa Hay (12% moisture), 240 lbs. of animal fat (0.3% moisture) and 30 lbs. supplement (i.e., vitamin and trace mineral supplement) (9% moisture).

Wet distiller grains are the first ingredient added to the mixer. A micro-ingredient container containing 105 g of monensin, pre-packaged according to an exemplary embodiment of the present invention, is placed in the mixer following the wet distiller grains. Wet corn gluten feed is then added to the mixer and the mixer contents are mixed for a period of time, for example 15 minutes. The moisture of these ingredients combined with the shearing effect of the mixer deteriorates and/or dissolves the film of the micro-ingredient container, releasing the contents (i.e., monensin) into the ingredient mixture. After a suitable mixing period, the rest of the ingredients are added and mixed, resulting in a TMR with 35 g/ton of monensin. The feed is then delivered to the cattle for consumption.

The disclosures of each and every patent, patent application, or publication cited herein are hereby incorporated by reference in their entirety. While this invention has been disclosed with reference to specific embodiments, other embodiments and variations of this invention may be devised by others skilled in the art without departing from the true spirit and scope of the invention. The appended claims are intended to be construed to include all such embodiments and variations.

The invention claimed is:

1. A method for preparing an animal feed mixture for livestock, comprising:
    providing a container comprising a water-soluble film, wherein an ionophore is sealed within the container,
    adding the container to a vessel with one or more feed components, and
    mixing the container with the one or more feed components in the vessel,
    wherein:
        at least a portion of the water-soluble film dissolves, ruptures, or deteriorates during mixing to release the ionophore,
        the ionophore is thoroughly dispersed throughout the animal feed mixture after mixing,
        the animal feed mixture is substantially solid,
        the ionophore is combined with the one or more feed components to form an animal feed mixture comprising an ionophore, and
        the ratio of the ionophore to the total amount of animal feed mixture is about 1:100 or less.

2. The method of claim 1, wherein a carrier or excipient is mixed with the ionophore prior to sealing within the container.

3. The method of claim 1, wherein the one or more feed components comprise protein, carbohydrate, fat, fiber, or a mixture thereof.

4. The method of claim 1, wherein the ratio of the ionophore to the total amount of animal feed mixture for livestock is about 1:1000 or less.

5. The method of claim 1, wherein the moisture content of the animal feed mixture for livestock is in the range of about 20 to 80%.

6. The method of claim 1, wherein the water-soluble film comprises a polyvinyl alcohol.

7. The method of claim 1, wherein the water-soluble film is suitable for ingestion by an animal.

8. The method of claim 1, wherein the ionophore is a pharmaceutical composition selected from the group consisting of a steroid, a beta-agonist, an antibiotic, and a vaccine.

* * * * *

UNITED STATES PATENT AND TRADEMARK OFFICE
CERTIFICATE OF CORRECTION

| | | |
|---|---|---|
| PATENT NO. | : 11,234,453 B2 | Page 1 of 1 |
| APPLICATION NO. | : 16/095866 | |
| DATED | : February 1, 2022 | |
| INVENTOR(S) | : Pike et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 612 days.

Signed and Sealed this
Eleventh Day of February, 2025

Coke Morgan Stewart
*Acting Director of the United States Patent and Trademark Office*